(12) United States Patent
Roettger et al.

(10) Patent No.: US 11,395,868 B2
(45) Date of Patent: Jul. 26, 2022

(54) DIALYSIS PRESCRIPTION OPTIMIZATION FOR DECREASED ARRHYTHMIAS

(71) Applicant: Medtronic, Inc., Minneapolis, MN (US)

(72) Inventors: Amy Roettger, Minneapolis, MN (US); VenKatesh R. Manda, Stillwater, MN (US); John Burnes, Coon Rapids, MN (US); Rebecca Poindexter, Minneapolis, MN (US); Martin T. Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 438 days.

(21) Appl. No.: 16/411,508

(22) Filed: May 14, 2019

(65) Prior Publication Data

US 2019/0262529 A1 Aug. 29, 2019

Related U.S. Application Data

(62) Division of application No. 15/333,267, filed on Oct. 25, 2016, now Pat. No. 10,335,534.

(Continued)

(51) Int. Cl.
*A61M 1/36* (2006.01)
*A61M 1/16* (2006.01)
(Continued)

(52) U.S. Cl.
CPC ....... *A61M 1/3609* (2014.02); *A61B 5/14546* (2013.01); *A61B 5/4839* (2013.01);
(Continued)

(58) Field of Classification Search
CPC . A61B 5/14546; A61B 5/4839; A61B 5/6866; A61B 5/7275; A61M 1/1696;
(Continued)

(56) References Cited

U.S. PATENT DOCUMENTS 3,602,222 A 8/1971 Herndon
3,608,729 A 9/1971 Haselden
(Continued)

FOREIGN PATENT DOCUMENTS

CN 101193667 6/2008
EP 266795 A2 11/1987
(Continued)

OTHER PUBLICATIONS

Australian Office Action for App. No. 2016349521, dated Aug. 31, 2020.
(Continued)

*Primary Examiner* — Benjamin J Klein (57) ABSTRACT

Systems and methods are provided for determining an estimated risk of arrhythmia during or after dialysis based on changes in serum potassium concentration of a patient and an amount of fluid removed from the patient during dialysis. The systems and methods allow for a determination of a risk that arrhythmia will occur due to the changes in potassium and fluid volume of a patient during dialysis, and for optimizing a dialysis prescription in order to minimize the risk of arrhythmia.

20 Claims, 5 Drawing Sheets

Related U.S. Application Data (60) Provisional application No. 62/252,375, filed on Nov. 6, 2015.

(51) Int. Cl.
*G16H 50/30* (2018.01)
*A61M 1/34* (2006.01)
*A61B 5/00* (2006.01)
*A61B 5/145* (2006.01)
*G16H 20/40* (2018.01)

(52) U.S. Cl.
CPC .......... *A61B 5/6866* (2013.01); *A61B 5/7275* (2013.01); *A61M 1/341* (2014.02); *A61M 1/3601* (2014.02); *G16H 20/40* (2018.01); *G16H 50/30* (2018.01); *A61M 1/1696* (2013.01); *A61M 2205/3334* (2013.01); *A61M 2230/005* (2013.01); *A61M 2230/04* (2013.01); *A61M 2230/20* (2013.01)

(58) Field of Classification Search
CPC .. A61M 1/341; A61M 1/3601; A61M 1/3609; A61M 2205/3334; A61M 2230/005; A61M 2230/04; A61M 2230/20; G16H 20/40; G16H 50/30
See application file for complete search history.

(56) References Cited

U.S. PATENT DOCUMENTS

| | | |
|---|---|---|
| 3,669,878 A | 6/1972 | Marantz |
| 3,669,880 A | 6/1972 | Marantz |
| 3,850,835 A | 11/1974 | Marantz |
| 3,884,808 A | 5/1975 | Scott |
| 3,989,622 A | 11/1976 | Marantz |
| 4,060,485 A | 11/1977 | Eaton |
| 4,371,385 A | 2/1983 | Johnson |
| 4,374,382 A | 2/1983 | Markowitz |
| 4,381,999 A | 5/1983 | Boucher |
| 4,460,555 A | 7/1984 | Thompson |
| 4,556,063 A | 12/1985 | Thompson |
| 4,562,751 A | 1/1986 | Nason |
| 4,581,141 A | 4/1986 | Ash |
| 4,650,587 A | 3/1987 | Polak |
| 4,678,408 A | 7/1987 | Mason |
| 4,685,903 A | 8/1987 | Cable |
| 4,750,494 A | 6/1988 | King |
| 4,799,493 A | 1/1989 | DuFault |
| 4,826,663 A | 5/1989 | Alberti |
| 4,828,693 A | 5/1989 | Lindsay |
| 5,080,653 A | 1/1992 | Voss |
| 5,092,886 A | 3/1992 | Dobos-Hardy |
| 5,097,122 A | 3/1992 | Coiman |
| 5,127,404 A | 7/1992 | Wyborny |
| 5,284,470 A | 2/1994 | Beltz |
| 5,302,288 A | 4/1994 | Meidl |
| 5,305,745 A | 4/1994 | Zacouto |
| 5,318,750 A | 6/1994 | Lascombes |
| 5,468,388 A | 11/1995 | Goddard |
| 5,683,432 A | 11/1997 | Goedeke |
| 5,762,782 A | 6/1998 | Kenley |
| 5,819,007 A | 10/1998 | Elghazzawi |
| 5,944,684 A | 8/1999 | Roberts |
| 5,987,352 A | 11/1999 | Klein |
| 6,048,732 A | 4/2000 | Anslyn |
| 6,052,622 A | 4/2000 | Holmstrom |
| 6,058,331 A | 5/2000 | King |
| 6,230,059 B1 | 5/2001 | Duffin |
| 6,248,093 B1 | 6/2001 | Moberg |
| 6,254,567 B1 | 7/2001 | Treu |
| 6,321,101 B1 | 11/2001 | Holmstrom |
| 6,362,591 B1 | 3/2002 | Moberg |
| 6,363,279 B1 | 3/2002 | Ben-Haim |
| 6,554,798 B1 | 4/2003 | Mann |
| 6,555,986 B2 | 4/2003 | Moberg |
| 6,589,229 B1 | 7/2003 | Connelly |
| 6,602,399 B1 | 8/2003 | Fromherz |
| 6,609,023 B1 | 8/2003 | Fischell |
| 6,627,164 B1 | 9/2003 | Wong |
| 6,676,608 B1 | 1/2004 | Keren |
| 6,711,439 B1 | 3/2004 | Bradley |
| 6,818,196 B2 | 11/2004 | Wong |
| 6,878,283 B2 | 4/2005 | Thompson |
| 6,960,179 B2 | 11/2005 | Gura |
| 7,077,819 B1 | 7/2006 | Goldau |
| 7,208,092 B2 | 4/2007 | Micheli |
| 7,276,042 B2 | 10/2007 | Polaschegg |
| 7,404,799 B1 | 7/2008 | Koh |
| 7,566,432 B2 | 7/2009 | Wong |
| 7,575,564 B2 | 8/2009 | Childers |
| 7,610,086 B1 | 10/2009 | Ke |
| 7,674,231 B2 | 3/2010 | McCombie |
| 7,704,361 B2 | 4/2010 | Garde |
| 7,736,507 B2 | 6/2010 | Wong |
| 7,754,852 B2 | 7/2010 | Burnett |
| 7,756,572 B1 | 7/2010 | Fard |
| 7,776,210 B2 | 8/2010 | Rosenbaum |
| 7,794,141 B2 | 9/2010 | Perry |
| 7,850,635 B2 | 12/2010 | Polaschegg |
| 7,867,214 B2 | 1/2011 | Childers |
| 7,922,686 B2 | 4/2011 | Childers |
| 7,922,911 B2 | 4/2011 | Micheli |
| 7,947,179 B2 | 5/2011 | Rosenbaum |
| 7,967,022 B2 | 6/2011 | Grant |
| 7,981,082 B2 | 7/2011 | Wang |
| 8,034,161 B2 | 10/2011 | Gura |
| 8,070,709 B2 | 12/2011 | Childers |
| 8,096,969 B2 | 1/2012 | Roberts |
| 8,183,046 B2 | 5/2012 | Lu |
| 8,187,250 B2 | 5/2012 | Roberts |
| 8,246,826 B2 | 8/2012 | Wilt |
| 8,273,049 B2 | 9/2012 | Demers |
| 8,292,594 B2 | 10/2012 | Tracey |
| 8,313,642 B2 | 11/2012 | Yu |
| 8,317,492 B2 | 11/2012 | Demers |
| 8,357,113 B2 | 1/2013 | Childers |
| 8,366,316 B2 | 2/2013 | Kamen |
| 8,366,655 B2 | 2/2013 | Kamen |
| 8,409,441 B2 | 4/2013 | Wilt |
| 8,499,780 B2 | 8/2013 | Wilt |
| 8,518,260 B2 | 8/2013 | Raimann |
| 8,535,525 B2 | 9/2013 | Heyes |
| 8,580,112 B2 | 11/2013 | Updyke |
| 8,597,227 B2 | 12/2013 | Childers |
| 8,696,626 B2 | 4/2014 | Kirsch |
| 8,903,492 B2 | 12/2014 | Soykan |
| 9,398,853 B2 | 7/2016 | Nanikashvili |
| 2002/0016550 A1 | 2/2002 | Sweeney |
| 2002/0042561 A1 | 4/2002 | Schulman |
| 2002/0112609 A1 | 8/2002 | Wong |
| 2003/0028089 A1 | 2/2003 | Galley |
| 2003/0069481 A1 | 4/2003 | Hervy |
| 2003/0080059 A1 | 5/2003 | Peterson |
| 2003/0097086 A1 | 5/2003 | Gura |
| 2003/0105435 A1 | 6/2003 | Taylor |
| 2003/0114787 A1 | 6/2003 | Gura |
| 2003/0187479 A1 | 10/2003 | TranThong |
| 2004/0019312 A1 | 1/2004 | Childers |
| 2004/0099593 A1 | 5/2004 | DePaolis |
| 2004/0147900 A1 | 7/2004 | Polaschegg |
| 2004/0215090 A1 | 10/2004 | Erkkila |
| 2005/0065760 A1 | 3/2005 | Murtfeldt |
| 2005/0113796 A1 | 5/2005 | Taylor |
| 2005/0126961 A1 | 6/2005 | Bissler |
| 2005/0126998 A1 | 7/2005 | Childers |
| 2005/0150832 A1 | 7/2005 | Tsukamoto |
| 2005/0234354 A1 | 10/2005 | Rowlandson |
| 2005/0234357 A1 | 10/2005 | Xue |
| 2005/0234381 A1 | 10/2005 | Niemetz |
| 2005/0234534 A1 | 10/2005 | Rowlandson |
| 2005/0274658 A1 | 12/2005 | Rosenbaum |
| 2006/0025661 A1 | 2/2006 | Sweeney |
| 2006/0217771 A1 | 2/2006 | Soykan |

(56) References Cited

U.S. PATENT DOCUMENTS

| | | |
|---|---|---|
| 2006/0191850 A1 | 8/2006 | Bosetto |
| 2006/0195064 A1 | 8/2006 | Plahey |
| 2006/0226079 A1 | 10/2006 | Mori |
| 2006/0241709 A1 | 10/2006 | Soykan |
| 2006/0247548 A1 | 11/2006 | Sarkar |
| 2006/0264894 A1 | 11/2006 | Moberg |
| 2007/0007208 A1 | 1/2007 | Brugger |
| 2007/0038138 A1 | 2/2007 | Gill |
| 2007/0066928 A1 | 3/2007 | Lannoy |
| 2007/0138011 A1 | 6/2007 | Hofmann |
| 2007/0175827 A1 | 8/2007 | Wariar |
| 2007/0179431 A1 | 8/2007 | Roberts |
| 2007/0215545 A1 | 9/2007 | Bissler |
| 2007/0255250 A1 | 11/2007 | Moberg |
| 2007/0276270 A1 | 11/2007 | Tran |
| 2008/0006570 A1 | 1/2008 | Gura |
| 2008/0021337 A1 | 1/2008 | Li |
| 2008/0053905 A9 | 3/2008 | Brugger |
| 2008/0067132 A1 | 3/2008 | Ross |
| 2008/0215247 A1 | 9/2008 | Tonelli |
| 2009/0020471 A1 | 1/2009 | Tsukamoto |
| 2009/0101577 A1 | 4/2009 | Fulkerson |
| 2009/0124869 A1 | 5/2009 | Hu |
| 2009/0127193 A1 | 5/2009 | Updyke |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2010/0004588 A1 | 1/2010 | Yeh |
| 2010/0010429 A1 | 1/2010 | Childers |
| 2010/0078381 A1 | 4/2010 | Merchant |
| 2010/0078387 A1 | 4/2010 | Wong |
| 2010/0084330 A1 | 4/2010 | Wong |
| 2010/0094158 A1 | 4/2010 | Solem |
| 2010/0114012 A1 | 5/2010 | Sandford |
| 2010/0137693 A1 | 6/2010 | Porras |
| 2010/0168546 A1 | 7/2010 | Kamath |
| 2010/0217181 A1 | 8/2010 | Roberts |
| 2010/0224492 A1 | 9/2010 | Ding |
| 2010/0234795 A1 | 9/2010 | Wallenas |
| 2010/0241045 A1 | 9/2010 | Kelly |
| 2011/0017665 A1 | 1/2011 | Updyke |
| 2011/0066006 A1 | 3/2011 | Banet |
| 2011/0066043 A1 | 3/2011 | Banet |
| 2011/0077574 A1 | 3/2011 | Sigg |
| 2011/0077575 A1 | 3/2011 | Kraemer |
| 2011/0079558 A1 | 4/2011 | Raimann |
| 2011/0087187 A1 | 4/2011 | Beck |
| 2011/0130666 A1 | 6/2011 | Dong |
| 2011/0137136 A1 | 6/2011 | Kotanko |
| 2011/0141116 A1 | 6/2011 | Dalesch |
| 2011/0184340 A1 | 7/2011 | Tan |
| 2011/0272337 A1 | 11/2011 | Palmer |
| 2011/0301447 A1 | 12/2011 | Park |
| 2011/0301472 A1 | 12/2011 | Grober |
| 2012/0016228 A1 | 1/2012 | Kroh |
| 2012/0083729 A1 | 4/2012 | Childers |
| 2012/0085707 A1 | 4/2012 | Beiriger |
| 2012/0115248 A1 | 5/2012 | Ansyln |
| 2012/0220528 A1 | 8/2012 | VanAntwerp |
| 2012/0258546 A1 | 10/2012 | Marran |
| 2012/0273354 A1 | 11/2012 | Orhan et al. |
| 2012/0273415 A1 | 11/2012 | Gerber |
| 2012/0273420 A1 | 11/2012 | Gerber |
| 2012/0277546 A1* | 11/2012 | Soykan .............. A61B 5/318 600/301 |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2012/0283581 A1 | 11/2012 | Olde et al. |
| 2012/0303079 A1 | 11/2012 | Mahajan |
| 2013/0037465 A1 | 2/2013 | Heyes |
| 2013/0116578 A1 | 5/2013 | An |
| 2013/0199998 A1 | 8/2013 | Kelly |
| 2013/0213890 A1 | 8/2013 | Kelly |
| 2013/0274642 A1 | 10/2013 | Soykan |
| 2013/0324915 A1 | 12/2013 | (Krensky)Britton |
| 2013/0330208 A1 | 12/2013 | Ly |
| 2013/0331774 A1 | 12/2013 | Farrell |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1* | 3/2014 | Soykan .............. A61B 5/0031 600/483 |
| 2014/0110340 A1 | 4/2014 | White |
| 2014/0110341 A1 | 4/2014 | White |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0217028 A1 | 8/2014 | Pudil |
| 2014/0217030 A1 | 8/2014 | Meyer |
| 2014/0220699 A1 | 8/2014 | Pudil |
| 2015/0144539 A1 | 5/2015 | Pudil |
| 2015/0148697 A1 | 5/2015 | Burnes |
| 2015/0149096 A1 | 5/2015 | Soykan |
| 2016/0023467 A1 | 1/2016 | Din et al. |

FOREIGN PATENT DOCUMENTS

| | | |
|---|---|---|
| EP | 1281351 | 2/2003 |
| EP | 1364666 A1 | 11/2003 |
| EP | 0906768 B1 | 2/2004 |
| EP | 1450879 | 10/2008 |
| EP | 1592494 B1 | 6/2009 |
| EP | 2100553 A1 | 9/2009 |
| EP | 2575827 A2 | 12/2010 |
| EP | 2100553 | 8/2011 |
| EP | 2576453 A2 | 12/2011 |
| EP | 2701580 | 11/2012 |
| EP | 2701595 | 11/2012 |
| EP | 1345856 B1 | 3/2013 |
| EP | 2344220 B1 | 4/2013 |
| EP | 2701596 | 3/2014 |
| EP | 2719406 B1 | 5/2016 |
| JP | S63-143077 | 11/1987 |
| JP | 5099464 | 10/2012 |
| WO | 9937342 | 7/1999 |
| WO | 0057935 | 10/2000 |
| WO | 200066197 A1 | 11/2000 |
| WO | 200170307 A1 | 9/2001 |
| WO | 2001085295 A2 | 9/2001 |
| WO | 2003043677 A2 | 5/2003 |
| WO | 2003043680 | 5/2003 |
| WO | 2003051422 A2 | 6/2003 |
| WO | 2004008826 | 1/2004 |
| WO | 2004009156 | 1/2004 |
| WO | 2004030716 A2 | 4/2004 |
| WO | 2004030717 A2 | 4/2004 |
| WO | 2004064616 A2 | 8/2004 |
| WO | 2005123230 A2 | 12/2005 |
| WO | 2007089855 A2 | 8/2007 |
| WO | 2009026603 | 12/2008 |
| WO | 2009026603 A1 | 3/2009 |
| WO | 2009157877 A1 | 12/2009 |
| WO | 2009157878 A1 | 12/2009 |
| WO | 2010028860 | 3/2010 |
| WO | 2010028860 A1 | 3/2010 |
| WO | 2011025705 A1 | 3/2011 |
| WO | WO2013022760 A1 | 8/2011 |
| WO | 2012148781 | 11/2012 |
| WO | 2012148786 | 11/2012 |
| WO | 2012148789 | 11/2012 |
| WO | 2012162515 A2 | 11/2012 |
| WO | 20120277551 | 11/2012 |
| WO | WO2012148788 A1 | 11/2012 |
| WO | 2012148784 | 12/2012 |
| WO | 2012172398 | 12/2012 |
| WO | 2013019179 A1 | 2/2013 |
| WO | 2013019994 A2 | 2/2013 |
| WO | 2013025844 | 2/2013 |
| WO | 2013028809 A3 | 2/2013 |

(56) References Cited

FOREIGN PATENT DOCUMENTS

| WO | 2013103607 A1 | 7/2013 |
| WO | 2013103906 | 7/2013 |
| WO | 2013114063 A1 | 8/2013 |
| WO | 2013121162 A1 | 8/2013 |
| WO | 14066254 | 5/2014 |
| WO | 14066255 | 5/2014 |
| WO | 14077082 | 5/2014 |
| WO | 2014121162 | 8/2014 |
| WO | 2014121163 | 8/2014 |
| WO | 2014121167 | 8/2014 |
| WO | 2014121169 | 8/2014 |
| WO | WO2015081221 A1 | 6/2015 |

OTHER PUBLICATIONS

[NPL105] Brynda, et al., The detection of toman 2-microglcbuiin by grating coupler immunosensor with three dimensional antibody networks. Biosensors & Bioelectronics, 1999, 363-368, 14(4).
[NPL10] Wheaton, et al., Dowex Ion Exchange Resins-Fundamentals of Ion Exchange; Jun. 2000, pp. 1-9. http://www.dow.com/scripts/litorder.asp?filepath=liquidseps/pdfs/noreg/177-01837.pdf.
[NPL111] Zhong, et al., Miniature urea sensor based on H(+)-ion sensitive field effect transistor and its application in clinical analysis, Chin. J. Biotechnol., 1992, 57-65. 8(1).
[NPL119] PCT/US2012/034331, International Search Report and Written Opinion dated Jul. 9, 2012.
[NPL121 ] Roberts M, The regenerative dialysis (REDY) sorbent system. Nephrology, 1998, 275-278:4.
[NPL138] U.S. Appl. No. 61/480,544.
[NPL139] U.S. Appl. No. 61/480,541 dated Apr. 29, 2011.
[NPL142] Hemametrics, Crit-Line Hematocrit Accuracy, 2003, 1-5, vol. 1, Tech Note No. 11 (Rev. D).
[NPL144] Weissman, S., et al., Hydroxyurea-induced hepatitis in human immunodeficiency virus-positive patients. Clin. Infec. Dis, (Jul. 29, 1999): 223-224.
[NPL146] PCT/US2012/034334, International Search Report, dated Jul. 6, 2012.
[NPL147] PCT/US2012/034335, International Search Report, dated Sep. 5, 2012.
[NPL148] PCT/US/2012/034327, International Search Report, dated Aug. 13, 2013.
[NPL149] PCT/US/2012/034329, International Search Report, dated Dec. 3, 2012.
[NPL14] Foley, et al., Long Interdialytic Interval and Martality among Patients Receiving Hemodialysis, N Engl Jrnl Med. 2011:365(12):1099-1107.
[NPL15] PCT International Search Report from International Application No. PCT/US2014/067650, dated Nov. 27, 2013.
[NPL169] Wang, Fundamentals of intrathoracic impedance monitoring in heart failure, Am. J. Cardiology, 2007, 3G-10G: Suppl.
[NPL16] PCT/US2014/067650 International Search Report Written Opinion dated Mar. 9, 2015.
[NPL170] Bleyer, et al, Kidney International. Jun. 2006; 69(12):2268-2273.
[NPL176] Bleyer, et al., Sudden and cardiac death rated in hemodialysis patients, Kidney International. 1999, 1553-1559: 55.
[NPL187] PCT/US2012/034333, International Preliminary Report on Patentability, dated Oct. 29, 2013.
[NPL188] PCT/US2012/034333, International Search Report, dated Aug. 29, 2012.
[NPL188] PCT/US2012/034333, International Search Report, dated Aug. 29, 2013.
[NPL197] PCT/US2012/034330, International Preliminary Report on Patentability, dated Oct. 29, 2013.
[NPL205] Culleton, Bf et al. Effect of Frequent Nocturnal Hemodialysis vs. Conventional Hemodialysis on Left Ventricular Mass and Quality of Life. 2007 Journal of the American Medical Association 298 (11), 1291-1299.

[NPL217] U.S. Appl. No. 13/757,722, filed Feb. 1, 2013.
[NPL218] U.S. Appl. No. 13/757,794, filed Feb. 2, 2012.
[NPL219] U.S. Appl. No. 13/791,755, filed Mar. 8, 2013.
[NPL21] U.S. Appl. No. 13/424,479 dated Nov. 1, 2012.
[NPL220] U.S. Appl. No. 13/757,792, filed Feb. 2, 2013.
[NPL222] U.S. Appl. No. 13/757,794, filed Feb. 2, 2013.
[NPL227] U.S. Appl. No. 13/837,287, filed Mar. 15, 2013.
[NPL22] U.S. Appl. No. 13/424,429 dated Nov. 1, 2012.
[NPL230] Redfield, et al., Restoration of renal response to atria! natriuretic factor in experimental low-output heat failure, Am. J. Physiol., Oct. 1, 1989, R917-923:257.
[NPL231] Rogoza, et al., Validation of A&D UA-767 device for the self-measurement of blood pressure, Blood Pressure Monitoring, 2000, 227-231, 5(4).
[NPL234] Lima, et al., An electrochemical sensor based on nanostructure hollsndite-type manganese oxide for detection of potassium ion, Sensors, Aug. 24, 2009, 6613-8625, 9.
[NPL235] MacLean, et al., Effects of hindlimb contraction on pressor and muscle interstitial metabolite responses in the cat, J. App. Physiol., 1998, 1583-1592, 85(4).
[NPL237] U.S. Appl. No. 13/757,693, dated Feb. 1, 2013.
[NPL238] PCT Application, PCT/US20013/020404, filed Jan. 4, 2013.
[NPL23] U.S. Appl. No. 13/424,525.
[NPL240] U.S. Appl. No. 13/836,973, filed Mar. 15, 2013.
[NPL241] U.S. Appl. No. 14/259,655, filed Apr. 23, 2014.
[NPL242] U.S. Appl. No. 14/259,589, filed Apr. 23, 2014.
[NPL264] PCT/US2014/014357 International Search Report and Written Opinion dated May 19, 2014.
[NPL268] Ronco et al. 2008, Cardiorenal Syndrome, Journal American College Cardiology, 52:1527-1539, Abstract.
[NPL26] Overgaard, et al., Activity-induced recovery of excitability in K+-depressed rat soleus muscle, Am. J. P 280: R48-R55, Jan. 1, 2001.
[NPL27] Overgaard et al., Relations between excitability and contractility in rate soleusmuscle: role of the NA+-K+ pump and NA+-K-S gradients. Journal of Physiology, 1999, 215-225, 518(1).
[NPL306] Coast, et al. 1990, An approach to Cardiac Arrhythmia analysis Using Hidden Markov Models, IEEE Transactions On Biomedical Engineering. 1990, 37(9):826-835.
[NPL309] Weiner, et al., Article: Cardiac Function and Cardiovascular Disease in Chronic Kidney Disease, Book: Primer on Kidney Diseases (Author: Greenberg, et al), 2009,499-505, 5th Ed., Saunders Elsevier, Philadelphia, PA.
[NPL310] U.S. Appl. No. 61/480,532.
[NPL311] U.S. Appl. No. 13/424,479.
[NPL312] U.S. Appl. No. 13/424,429 dated Nov. 1, 2012.
[NPL313] U.S. Appl. No. 13/424,525.
[NPL317] U.S. Appl. No. 61/480,530.
[NPL318] U.S. Appl. No. 61/480,528 dated Apr. 29, 2011.
[NPL328] Genovesi, et al., Nephrology, Dialysis, Transplantation 2009; 24(8):2529-2536.
[NPL32] Secemsky, et al, High prevalence of cardiac autonomic dysfunction and T-wave alternans in dialysis patients. Heart Rhythm, Apr. 2011, 592-598: vol. 8, No. 4.
[NPL35] Wei, et al., Fullerene-cryptand coated piezoelectric crystal urea sensor based on urease, Analytica Chimica Acta, 2001,77-85:437.
[NPL376] Gambro AK 96 Dialysis Machine Operators Manual, Dec. 2012. p. 1-140.
[NPL37] U.S. Appl. No. 13/368,225 dated Feb. 7, 2012.
[NPL383] Leifer et al., A Study on the Temperature Variation of Rise Velocity for Large Clean Bubbles, J. Atmospheric & Oceanic Tech., vol. 17, pp. 1392-1402, Oct. 2000.
[NPL384] Talaia, Terminal Velocity of a Bubble Rise in a Liquid Column, World Acad. of Sci., Engineering & Tech., vol. 28, pp. 264-268, Published Jan. 1, 2007.
[NPL386] The FHN Trial Group. In-Center. Hemodialysis Six Times per Week versus Three Times per Week, New England Journal of Medicine, 2010 Abstract.
[NPL39] PCT/US2012/034332, International Search Report, dated Jul. 5, 2012.

(56) References Cited

OTHER PUBLICATIONS

[NPL46] Siegenthaler, et al., Pulmonary fluid status monitoring with intrathoracic impedance, Journal of Clinical Monitoring and Computing, 24:449-451, published Jan. 12, 2011.
[NPL47] U.S. Appl. No. 61/480,544.
[NPL55] U.S. Appl. No. 13/424,454.
[NPL57] U.S. Appl. No. 13/424,467.
[NPL62] U.S. Appl. No. 13/424,533.
[NPL632] Lakerveld et al, Primary prevention of diabetes mellitus type 2 and cardiovascular diseases using a cognitive behavior program aimed at lifestyle changes in people at risk: Design of a randomized controlled trial, 2008, BMC Endocrine Disorders, 8(6): 1-19.
[NPL633] Gordhandas et al, Real-Time Extraction and Analysis of Key Morphological Features in the Electrocardiogram, for Data Compression and Clinical Decision Support, 2004, Computational Physiology, pp. 15-18.
[NPL67] U.S. Appl. No. 13/424,490.
[NPL68] U.S. Appl. No. 13/424,517.
[NPL81] U.S. Appl. No. 61/480,539 dated Apr. 29, 2011.
[NPL84] U.S. Appl. No. 61/480,535 dated Apr. 29, 2011.
[NPL90] Nedelkov, et al., Design of buffer exchange surfaces and sensor chips for biosensor chip mass spectrometry, Proteomics, 2002, 441-446, 2(4).
[NPL] European Search Report App 14865374.4, dated Jun. 12, 2017.
[NPL] European Search Report for Application No. 14865128.4 dated Jun. 20, 2017.
[NPL] Green et al., Sudden Cardiac Death in Hemodialysis Patients: an In-Depth Review , Am J Kidney Dis 57(6)921:929.
[NPL] Rajan et al. Generalized Feature Extraction for Time-Varying Autoregressive Models, IEEE Transacion Signal Processing vol. 44, No. 10.
Chinese Office Action in App. No. 201480059332.5, dated Mar. 30, 2018.
EP OA for App. No. 16709165.1 dated Oct. 22, 2019.
European Search Report for App. No. 14859115.9, dated Jan. 5, 2018.
Laurent, Jeanpierre, "Continuous Monitoring of Dynamic Systems: Application to Monitoring of Dialyzed Patients" Oct. 30, 2004, received from internet: http://laurent.jeanpierre1.free.fr/recherche/papiers/aista2004.pdf.
PCT/US2016/058579 International Search Report dated Jan. 31, 2017.
PCT/US2016/058579_WO.

* cited by examiner

DIALYSIS PRESCRIPTION OPTIMIZATION FOR DECREASED ARRHYTHMIAS

CROSS-REFERENCE TO RELATED APPLICATIONS

This application claims the benefit of and priority to U.S. Provisional Patent Application No. 62/252,375 filed Nov. 6, 2015, the entire disclosure of which is incorporated by reference herein.

FIELD OF THE INVENTION

The invention relates to devices, systems, and methods for calculating a risk of cardiac arrhythmia due to changes in potassium concentration and fluid levels of a patient during dialysis. The invention also relates to devices, systems, and methods for optimizing dialysis parameters in order to reduce the risk of arrhythmia.

BACKGROUND

Cardiac arrhythmia is an important contributor to cardiovascular morbidity and mortality in dialysis patients. Available technology has previously limited the ability to determine the burdens and triggers of cardiac arrhythmia in dialysis patients. An observational study has shown that the rate of cardiac arrhythmia in dialysis patients is influenced by both the amount of fluid removed from the patient during dialysis and the intradialytic change in potassium concentration.

There is a need for systems and methods capable of determining the probability that a dialysis patient will suffer a cardiac arrhythmia event based on the changes to potassium concentration in the patient during dialysis, as well as the amount of fluid removed from the patient during dialysis. There is a further need for a system that can optimize a dialysis prescription, and in particular, optimize the amount of fluid removed from the patient and the change in potassium concentration in the patient in order to minimize the risk of cardiac arrhythmia. There is a further need for systems and methods capable of determining the risk of cardiac arrhythmia in a patient after dialysis in order to mitigate the effects of any resulting arrhythmias.

SUMMARY OF THE INVENTION

The first aspect of the invention relates to a method for setting an ultrafiltration rate or potassium concentration of a dialysate in a dialysis session. In any embodiment of the first aspect of the invention, the method comprises determining a potassium concentration of a patient; determining a fluid volume of the patient; calculating a desired potassium concentration change and a desired fluid volume change for a dialysis session, wherein the desired potassium concentration change and desired fluid volume change are calculated based on a first risk score for arrhythmia due to an anticipated change in potassium concentration and an anticipated change in fluid volume during dialysis; and setting an ultrafiltration prescription and/or a potassium prescription based on the desired potassium concentration change and desired fluid volume change.

In any embodiment of the first aspect of the invention, the desired potassium concentration change and desired fluid volume change can be calculated in order to result in the first risk score for arrhythmia that is below a predetermined level.

In any embodiment of the first aspect of the invention, the first risk score for arrhythmia is calculated using an algorithm.

In any embodiment of the first aspect of the invention, the step of calculating a risk score for arrhythmia uses a lookup table.

In any embodiment of the first aspect of the invention, the method comprises the step of monitoring a patient potassium concentration and/or an amount of fluid removed from the patient during dialysis, and calculating a second risk score for arrhythmia based on the monitored potassium concentration and/or amount of fluid removed during dialysis.

In any embodiment of the first aspect of the invention, the method comprises altering the potassium prescription or ultrafiltration prescription based on the second risk score.

The features disclosed as being part of the first aspect of the invention can be in the first aspect of the invention, either alone or in combination, or follow a preferred arrangement of one or more of the described elements.

The second aspect of the invention is directed to a system. In any embodiment of the second aspect of the invention, the system comprises a dialysate flow loop comprising a dialyzer; wherein dialysate enters the dialyzer through a dialysate inlet and exits the dialyzer through a dialysate outlet; an extracorporeal flow loop for transporting blood from a patient, to the dialyzer, and back to the patient; an ultrafiltration pump, wherein the ultrafiltration pump controls a net fluid movement between a patient and the dialysate flow loop; control electronics, wherein the control electronics are configured to control a pump rate of the ultrafiltration pump; a processor; wherein the processor is configured to obtain a potassium concentration of a patient; the processor configured to calculate a risk score for arrhythmia, wherein the risk score for arrhythmia is based at least in part on the potassium concentration of the patient and a fluid volume of the patient; and wherein the processor calculates an ultrafiltration prescription based on the risk score for arrhythmia and transmits the ultrafiltration prescription to the control electronics; and wherein the control electronics are configured to control the pump rate of the ultrafiltration pump based on the ultrafiltration amount.

In any embodiment of the second aspect of the invention, the system comprises a potassium reservoir fluidly connected to the dialysate flow rate and a potassium pump; wherein the control electronics are configured to control a pump rate of the potassium pump; the potassium pump configured to control an addition of potassium from the potassium reservoir to the dialysate to create a determined dialysate potassium concentration; wherein the processor is configured to calculate the determined dialysate potassium concentration based on the risk score for arrhythmia.

In any embodiment of the second aspect of the invention, the processor can calculate the risk score of arrhythmia based on a lookup table.

In any embodiment of the second aspect of the invention, the processor can calculate the risk score of arrhythmia based on an algorithm.

In any embodiment of the second aspect of the invention, the processor can calculate the determined potassium concentration of the dialysate and/or the ultrafiltration prescription to result in a risk score of less than a predetermined level.

In any embodiment of the second aspect of the invention, the processor can calculate the ultrafiltration prescription to result in a risk score of less than a predetermined level.

In any embodiment of the second aspect of the invention, the predetermined level can manage a risk of arrhythmia to be estimated at less than or equal to 0.02 instances of arrhythmia per hour.

In any embodiment of the second aspect of the invention, the system comprises a potassium sensor positioned in the dialysate flow loop.

In any embodiment of the second aspect of the invention, the processor can be configured to obtain a potassium concentration of the patient during dialysis.

In any embodiment of the second aspect of the invention, the processor can be configured to calculate an updated determined potassium concentration in the dialysate or ultrafiltration prescription based on the potassium concentration of the patient during dialysis.

In any embodiment of the second aspect of the invention, the processor can be configured to continuously receive a potassium concentration of the patient during a dialysis session.

In any embodiment of the second aspect of the invention, the potassium concentration of a patient can be determined based at least in part on a potassium concentration in the dialysate downstream of the dialyzer.

The features disclosed as being part of the second aspect of the invention can be in the second aspect of the invention, either alone or in combination, or follow a preferred arrangement of one or more of the described elements.

The third aspect of the invention is directed to a method for calculating a risk score indicative of a probability of cardiac arrhythmia. In any embodiment of the third aspect of the invention, the method comprises measuring a change in potassium concentration of a patient during dialysis to calculate a risk score for cardiac arrhythmia during or after dialysis; measuring a fluid volume removed from the patient during dialysis; and calculating a risk score for arrhythmia for the patient; wherein the risk score is indicative of a probability of cardiac arrhythmia.

In any embodiment of the third aspect of the invention, the method comprises the step of calculating a change in potassium concentration during dialysis based on a pre-dialysis potassium concentration and a post-dialysis potassium concentration.

In any embodiment of the third aspect of the invention, the step of calculating a risk score for arrhythmia uses an algorithm.

In any embodiment of the third aspect of the invention, the method comprises the step of measuring the change in potassium concentration of a patient using any one of an implantable loop recorder, implantable defibrillator, implantable cardiac monitor, blood analysis, ion-selective electrode, or flame photometer.

The features disclosed as being part of the third aspect of the invention can be in the third aspect of the invention, either alone or in combination, or follow a preferred arrangement of one or more of the described elements.

DETAILED DESCRIPTION OF THE INVENTION

Unless defined otherwise, all technical and scientific terms used generally have the same meaning as commonly understood by one of ordinary skill in the art.

The articles "a" and "an" are used to refer to one or to over one (i.e., to at least one) of the grammatical object of the article. For example, "an element" means one element or over one element.

The term "algorithm" refers to a set of self-contained step-by-step operations to be performed to solve a problem or complete a process. An algorithm can contain one or more equations, and can also be a computer program.

The term "altering the potassium prescription," or to "alter the potassium prescription" refers to the process of changing an initially determined potassium prescription. In any embodiment, a potassium prescription can be altered during dialysis, and the described systems can automatically carry out the altered potassium prescription.

An "anticipated change in fluid volume" refers to a predicted or estimated change in the fluid volume of a patient that will occur during a dialysis session.

An "anticipated change in potassium concentration" refers to a predicted or estimated change in the potassium concentration of a patient that will occur during a dialysis session.

An "arrhythmia" or "arrhythmia event" is a condition wherein a subject's heart beats at an abnormal rhythm. As used herein, arrhythmia can refer to atrial fibrillation, atrial flutter, ventricular fibrillation, ventricular tachycardia, bradyarrhythmia, or any type of arrhythmia known in the art.

The term "based in part" refers to a calculation or determination comprising at least the noted variables. In any embodiment, other variables may be included in the calculation or determination, however, the noted variables must be used.

The term "blood analysis" refers to determining the concentration of a solute in the blood of a patient by directly measuring the concentration in a sample of blood.

The term "calculating," or "to calculate" refers to the process of determining a given value mathematically. The process can be implemented using specifically purposed computers, processors, software, and the like.

The term "comprising" includes, but is not limited to, whatever follows the word "comprising." Use of the term indicates the listed elements are required or mandatory but that other elements are optional and may be present.

The term "configured to obtain" refers to the ability of a component to receive information.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The term "continuously receive" refers to the ability of a component to receive information repeatedly. In any embodiment, the term "continuously receive" can refer to the ability to receive information constantly and in real-time. However, the term "continuously receive" can also refer to the ability to receive information at short intervals.

The term "control" or "configured to control" refers to the ability of one component to direct the actions of a second component.

The term "control electronics" refers to combinations of components that act together to maintain a system to a desired set of performance specifications. The control electronics can use processors, memory and computer components configured to interoperate to maintain the desired performance specifications.

A "desired fluid volume change" is a value indicative of the difference between a pre-dialysis fluid volume of a patient and a post-dialysis fluid volume of a patient, wherein the post-dialysis fluid volume of a patient is set at some level in order to optimally treat the patient A "desired potassium concentration change" is a value indicative of the difference between a pre-dialysis potassium concentration of a patient and a post-dialysis potassium concentration of a patient, wherein the post-dialysis potassium concentration of a patient is set at some level in order to optimally treat the patient.

A "determined dialysate potassium concentration" refers to a concentration of potassium in a dialysate that is set to some value.

"Determining a fluid volume of a patient" refers to calculating a total amount of either intra-, or extracellular fluid in the patient, or both intra- and extracellular fluid combined.

"Determining a potassium concentration of a patient" refers to calculating the amount of potassium in the blood of a patient at any given point in time. The potassium concentration can be defined in terms of mmol/L, mEq/L, or any other value that provides the amount of potassium in the blood of the patient.

The term "dialysate" describes a fluid into or out of which solutes from a fluid to be dialyzed diffuse through a membrane.

The term "dialysate inlet" refers to the portion of a dialyzer into which dialysate enters the dialyzer.

A "dialysate outlet" is the portion of a dialyzer from which dialysate exits the dialyzer.

The term "dialysate flow loop" refers to the path through which dialysate can travel during dialysis.

A "dialysis session" is period of time that a patient is treated by dialysis, hemodialysis, hemofiltration, ultrafiltration, combinations thereof, or other blood fluid removal therapy.

The term "dialyzer" refers to a cartridge or container with two flow paths separated by semi-permeable membranes. The membranes can be in the form of hollow fibers, flat sheets, or spiral wound or other conventional forms known to those of skill in the art. Membranes can be selected from the following materials of polysulfone, polyethersulfone, poly(methyl methacrylate), modified cellulose, or other materials known to those skilled in the art.

The term "downstream" refers to a position of a first component in a flow path relative to a second component wherein fluid will pass by the second component prior to the first component during normal operation. The first component can be said to be "downstream" of the second component, while the second component is "upstream" of the first component.

The term "extracorporeal flow loop" refers to a fluid pathway incorporating one or more components such as but not limited to conduits, valves, pumps, fluid connection ports or sensing devices configured therein such that the pathway conveys blood from a subject to an apparatus for hemodialysis, hemofiltration, hemodiafiltration or ultrafiltration and back to the subject.

A "flame photometer" is a device that measures the spectral lines in a vaporized solution in order to determine the concentration of metal ions in the solution.

The term "fluid volume of a patient" refers to the total amount of intra- and extracellular fluid in the patient.

The term "fluid volume removed from a patient" refers to the amount of fluid removed from a patient during a dialysis session.

The term "fluid connection," "fluidly connectable," and "fluidly connected" refers to the ability to pass fluid or gas from one point to another point. The two points can be within or between any one or more of compartments, modules, systems, and components, all of any type.

An "implantable cardiac monitor" is a device implantable into a patient that can monitor the electrical activity of the patient's heart.

An "implantable defibrillator" is a device implantable into a patient that can monitor the electrical activity of the patient's heart and perform cardioversion, defibrillation and pacing of the heart.

An "implantable loop recorder" is a device implantable into a patient that can monitor and record the electrical activity of the patient's heart.

An "ion-selective electrode" is a sensor that converts the activity of a specific ion dissolved in a solution into an electrical potential, which can be measured by a voltmeter or pH meter and used to determine the concentration.

The term "lookup table" refers to an electronic table correlating the effects of changing a particular variable or variables on a given outcome.

The term "manages the risk of arrhythmia" or to "manage the risk of arrhythmia" refers to the process of causing the risk of arrhythmia to be at or below some predetermined level.

The term "measuring a change in potassium concentration of a patient" or to "measure a change in potassium concentration of a patient" refers to making a calculation of the difference between a pre-dialysis potassium concentration in the patient and a post-dialysis potassium concentration in the patient.

The term "measuring a fluid volume removed from the patient" or to "measure a fluid volume removed from the patient" refers to making a calculation of the difference between a pre-dialysis fluid level of the patient and the post-dialysis fluid level of the patient.

The term "monitoring a patient potassium concentration," or to "monitor a patient potassium concentration" refers to the process of measuring the potassium concentration of a patient during a dialysis session.

The term "monitoring an amount of fluid removed from the patient," or to "monitor an amount of fluid removed" refers to the process of measuring the amount of fluid removed from a patient during a dialysis session.

The term "post-dialysis potassium concentration" refers to the concentration of potassium in a patient after the patient undergoes dialysis.

The term "potassium concentration of a patient" refers to the amount of potassium in the blood of a patient at any given point in time. The potassium concentration can be defined in terms of mmol/L, mEq/L, or any other value that provides the amount of potassium in the blood of the patient.

The term "potassium prescription" refers to a preset or desired change or value in potassium concentration of a patient during a dialysis session.

A "potassium pump" is a pump connected to a potassium reservoir, wherein the potassium pump controls the movement of fluid between the potassium reservoir and a dialysate flow path.

A "potassium reservoir" is a container of any type that contains a solution of potassium ions.

A "potassium sensor" is a component that is capable of determining the potassium concentration in a fluid.

The term "predetermined level" or "predetermined number" refers to a value for a given parameter that is determined prior to the dialysis session.

The term "pre-dialysis potassium concentration" refers to the potassium concentration of a patient prior to undergoing dialysis treatment.

A "probability of cardiac arrhythmia" refers to any value that is correlated to the chances that a cardiac arrhythmia will occur in a given time period.

The term "processor" as used herein is a broad term and is to be given its ordinary and customary meaning to a person of ordinary skill in the art. The term refers without limitation to a computer system, state machine, processor, or the like designed to perform arithmetic or logic operations using logic circuitry that responds to and processes the basic instructions that drive a computer. In any embodiment of the first, second, third, and fourth invention, the terms can include ROM ("read-only memory") and/or RAM ("random-access memory") associated therewith.

The term "pump rate" refers to the volume of fluid that a pump conveys per unit of time.

A "risk score for arrhythmia" is a numerical value indicative of the probability that an arrhythmia will occur in a patient. In any embodiment, the risk score for arrhythmia can be calculated as a probability of arrhythmia, or instead can be calculated as an estimated number of arrhythmias the patient will experience in a given time frame.

"Setting" a dialysis prescription, ultrafiltration prescription, potassium prescription, or similar, generally refers to placing, adjusting, or facilitating any set of parameters required for a particular patient for the specified dialysis, ultrafiltration, potassium prescription to be achieved during a therapy session.

The term "ultrafiltration prescription" refers to the amount of fluid to be removed from a patient during a dialysis session, and/or the rate of fluid removal from the patient.

An "ultrafiltration pump" is a pump capable of controlling the rate of ultrafiltration from a patient during dialysis by controlling the net fluid movement between the blood side and dialysate side of the dialyzer.

An "updated determined potassium concentration in the dialysate" refers to a second calculation of a determined potassium concentration in the dialysate using information not available or not used during an initial calculation of the determined potassium concentration in the dialysate.

An "updated ultrafiltration prescription" refers to a second determination of an ultrafiltration prescription using information not available or not used during an initial determination of an ultrafiltration prescription.

Arrhythmia Risk

The first, second, and third aspects of the invention relate to systems and methods for determining a risk of cardiac arrhythmia based on an intradialytic change in fluid volume and potassium concentration of a patient, as well as system and methods to prevent an increased risk of cardiac arrhythmia during and after dialysis.

The risk of cardiac arrhythmia during and after dialysis is affected by both a change in potassium concentration for a patient and an amount of fluid removed from the patient during the dialysis session. In order to lessen the risk of cardiac arrhythmia, the change in potassium concentration in a patient and the amount of fluid removed from the patient can be controlled.

Figure 1:
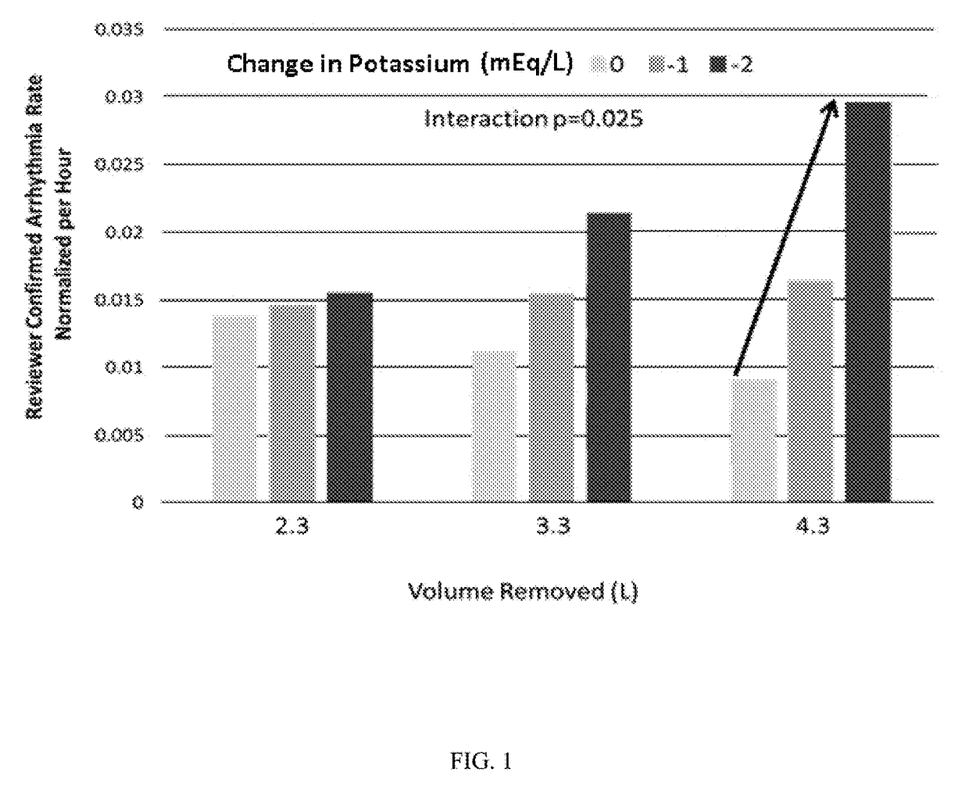
FIG. 1 shows a graphical representation of the effects of fluid removal and change in potassium concentration on the frequency of cardiac arrhythmia for patients undergoing dialysis treatment.

FIG. 1 shows a graphical representation of the effects of fluid removal and change in potassium concentration on the frequency of cardiac arrhythmia for patients undergoing dialysis treatment. As illustrated by FIG. 1, the rate of cardiac arrhythmia is related to the amount of potassium removed at any of the illustrated levels of fluid removal. That is, cardiac arrhythmia is more likely to occur when the concentration of potassium in the patient has decreased by a greater amount. This effect is increased with increasing fluid removal. The more fluid removed from a patient during dialysis, the greater the change in the rate of cardiac arrhythmias as dependent upon the change in potassium level of the patient. FIG. 1 also illustrates that the rate of cardiac arrhythmia is generally proportional to the amount of fluid removed from a patient during dialysis. Where the change in patient potassium level is at least one mEq/L, the rate of cardiac arrhythmia increases with increasing fluid removal.

Figure 2:
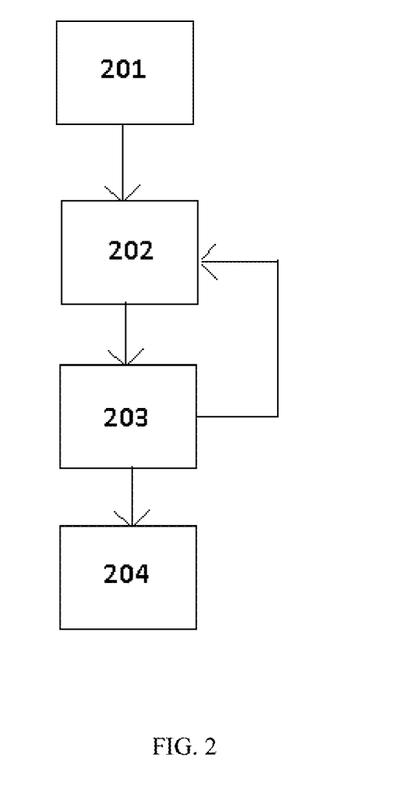
FIG. 2 shows a flow chart illustrating the steps that can be used to determine a potassium prescription and an ultrafiltration prescription.

In any embodiment of the first, second, or third aspects of the invention, a risk score can be calculated corresponding to a probability of arrhythmia due to the changes in potassium levels and fluid levels of a patient during dialysis. As shown in FIG. 2, this risk score can be used to determine an optimal dialysis prescription in order to minimize the risk of cardiac arrhythmia. In order to calculate an optimal dialysis prescription, a fluid volume and potassium concentration of a patient can be determined prior to dialysis at step 201. In any embodiment of the first, second, or third, aspects of the invention, the potassium concentration of the patient can be the serum potassium concentration of the patient. The potassium concentration of a patient can be determined by any method known in the art, including but not limited to a blood analysis, an implantable loop recorder, an implantable defibrillator, or an implantable cardiac monitor. Changes in an ECG for a patient, such as would be monitored by an implantable or non-implantable loop recorder, defibrillator or cardiac monitor can be used to determine changes in potassium concentration of a patient. The potassium concentration of the patient can also be determined using flame photometer or ion-selective electrode. In any embodiment of the first, second, or third aspects of the invention, a blood line can be connected from the patient or an extracorporeal flow loop during dialysis to a potassium monitor, such as a potassium ion selective electrode or a flame photometer. One of skill in the art will understand that the total potassium concentration in a patient or the serum potassium concentration of a patient can be determined in other ways known in the art, all of which are within the scope of the invention. In any multiple methods of determining the potassium concentration in a patient can be used and compared or averaged for increased accuracy. In any embodiment of the first, second, or third aspects of the invention, a feedback loop can be provided for the potassium concentration of a patient, providing real-time or repeated measurements of the potassium concentration of the patient. The fluid volume of a patient can be determined by any method known in the art, including impedance measurements and comparisons of a patient's weight to a known or estimated dry weight of the patient. Based on the calculated fluid volume, an initial desired fluid volume change for the patient during the dialysis session can be determined at step 202. The initial desired fluid volume change is an anticipated fluid volume change that will occur during dialysis if no other modifications are made. Based on a desired ending potassium level for the patient, an initial desired potassium concentration change for the patient during the dialysis session can also be calculated at step 202. The initial desired potassium concentration change is an anticipated potassium concentration change that will occur during dialysis if no other modifications are made. Using the anticipated fluid volume change and the anticipated potassium concentration changed, a risk score for arrhythmia can be calculated at step 203, as explained herein, wherein the risk score is indicative of a risk of cardiac arrhythmia in the patient. A determination can be made whether the risk score calculated in step 203 is acceptable. If the risk score is acceptable, the dialysis prescription can be set as explained herein in order to remove the desired amount of fluid from the patient and to effect the desired change in potassium concentration for the patient. If the risk score calculated in step 203 is unacceptable, meaning that the risk of cardiac arrhythmia is higher than some predetermined value, the desired potassium concentration change and desired fluid volume change can be varied, such as by using a smaller potassium concentration change or smaller fluid volume change in step 202. The new desired potassium concentration change can provide a new anticipated potassium concentration change, and the new desired fluid volume change can provide a new desired fluid volume change. After varying the desired potassium concentration change and fluid volume change in step 202 a new anticipated potassium concentration change and a new anticipated fluid volume change can be used to calculate a new risk score again in step 203. The process can be repeated until the risk score for cardiac arrhythmia is calculated to be less than some predetermined level. The desired fluid volume change can be used to set an ultrafiltration prescription, or the amount and rate at which fluid will be removed from the patient during a dialysis session. The desired potassium concentration change can be used to set a potassium prescription, or the amount by which the potassium concentration of the patient will change during a dialysis session.

One of ordinary skill in the art will understand, that once an ultrafiltration prescription and potassium prescription are set, there are several methods to achieve the desired changes. The amount of fluid removed from a patient can be altered by changing the rate at which ultrafiltrate is removed from the blood of the patient. The potassium concentration in a patient can be altered by changing the concentration of potassium in the dialysate, changing the blood flow rate during dialysis, or changing the dialysate flow rate during dialysis. These methods, or any other methods of achieving a particular change in potassium concentration and a particular change in fluid volume for the patient are within the scope of this invention. In any embodiment of the first, second, or third aspects of the invention, the ultrafiltration prescription and/or potassium prescription can be set by a processor, as described herein. The processor, after determining the desired change in fluid volume and the desired change in potassium concentration, can set an ultrafiltration prescription and a potassium prescription to achieve these desired changes. The processor can then transmit the prescriptions or instructions for achieving the prescribed changes to control electronics in order to carry out the determined prescriptions, as described herein. In any embodiment of the first, second, or third aspects of the invention, the ultrafiltration prescription and potassium prescription can be set by a user as opposed to a processor. One of skill in the art will understand how to set a dialysis prescription based on the desired changes in potassium concentration and fluid volume, such as by controlling the pump rate of an ultrafiltration pump or by changing the potassium concentration of the dialysate.

In any embodiment of the first, second, or third aspects of the invention, the amount of fluid removed from the patient, and the potassium concentration of the patient can be monitored during dialysis. The monitored values can be used to calculate a second risk score based on the actual results during dialysis. If the monitored values deviate from the prescription determined prior to dialysis, the described methods can include altering the ultrafiltration prescription and/or potassium prescription to ensure that the patient risk score for arrhythmia does not cross the predetermined level. In any embodiment of the first, second, or third aspects of the invention, the amount of fluid removed from the patient and the potassium concentration of the patient can be continuously monitored, and new risk scores can be continuously calculated. This allows the ultrafiltration and potassium prescriptions to be continuously updated and the ultrafiltration rate and potassium concentration in the dialysate to be continuously adjusted based on real-time analysis of the risk scores.

In any embodiment of the first, second, or third aspects of the invention, the potassium concentration in the dialysate can be changed at a predetermined time and by a predetermined amount. For example, at some point during the dialysis session, the potassium concentration in the dialysate can be changed from 0 mEq/L to 2 mEq/L during a dialysis session in order to better control the changes in patient potassium concentration. In any embodiment of the first, second, or third aspects of the invention, the change in potassium concentration in the dialysate can occur at any point during the dialysis session, including at or near the half-way point of the dialysis session. In any embodiment of the first, second, or third aspects of the invention, the potassium concentration of the dialysate can be changed by any amount, including from between 0 mEq/L to 2 mEq/L, from 0 mEq/L to 1 mEq/L, or from 1 mEq/L to 2 mEq/L. In any embodiment of the first, second or third aspects of the invention, the potassium concentration of the dialysate can be changed from 2 mEq/L to 0 mEq/L, from 2 mEq/L to 1 mEq/L or from 1 mEq/L to 0 mEq/L. One of ordinary skill in the art will understand that other predetermined adjustments to the potassium concentration can be made at various times during a dialysis session in order to better control the changes in patient potassium concentration.

In any embodiment of the first, second, or third aspects of the invention, the system can be used to calculate a risk score for arrhythmia after a dialysis session by measuring the change in potassium concentration of the patient during dialysis and measuring the fluid volume removed from the patient during dialysis. The change in potassium concentration during dialysis can be calculated as the difference between the pre-dialysis potassium concentration for the patient and the post-dialysis potassium concentration of the patient. Calculation of a risk score for arrhythmia after a dialysis session can be useful in order to minimize the adverse affects of arrhythmias due to changes during dialysis. For example, if after dialysis a patient is determined to be at high risk for arrhythmia, increased monitoring can be used to ensure that any arrhythmia events are immediately treated.

Figure 3:
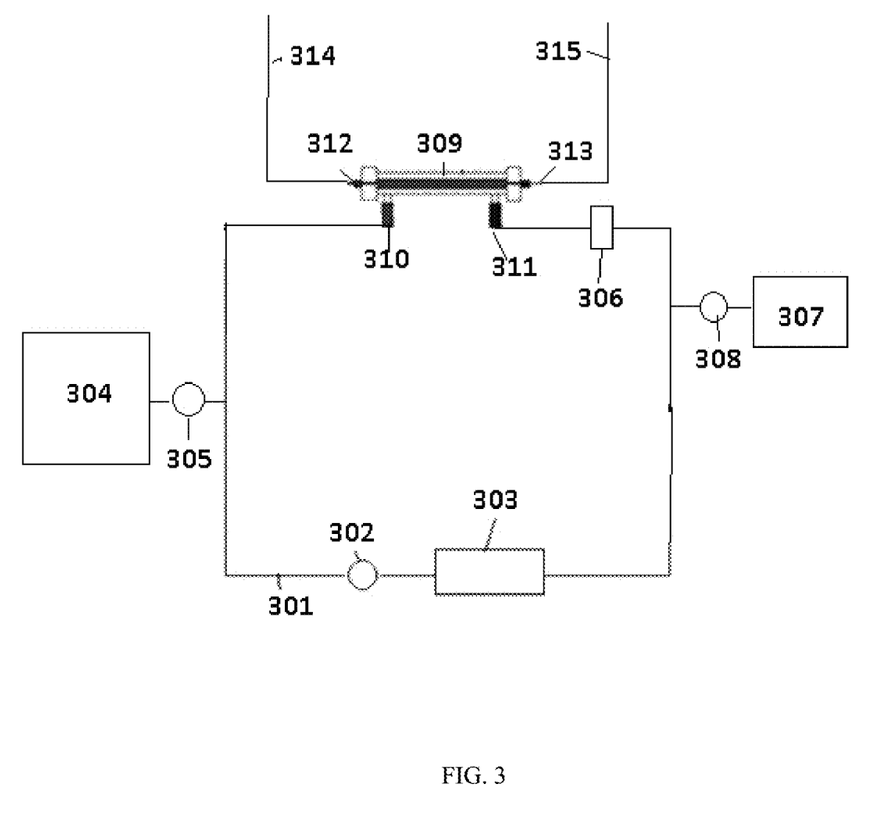
FIG. 3 is a representative drawing of a dialysis flow loop capable of carrying out the described invention.

FIG. 3 shows a simplified dialysate flow loop for use with the systems and methods of the described invention. Dialysate can travel through the dialysate flow loop 301. Dialysate pump 302 provides the force necessary to move dialysate through the dialysate flow loop 301, and also controls the dialysate flow rate. Dialysate enters a dialyzer 309 through dialysate inlet 311 and exits the dialyzer 309 through dialysate outlet 310. At the same time, blood is transported through an extracorporeal flow loop from a patient, through arterial patient line 314 and enters the dialyzer 309 through blood inlet 312. Blood exits the dialyzer 309 through blood outlet 313 and is returned to the patient through venous blood line 315. The dialyzer is separated into a blood side and a dialysate side by a semi-permeable membrane (not shown). Solutes and fluid can travel through the semi-permeable membrane from the blood to the dialysate or from the dialysate to the blood. The direction and rate at which solutes will pass through the semi-permeable membrane is due in part to a concentration gradient that exits between the blood and the dialysate. As such, by changing the concentration of a particular solute in the dialysate, the movement of that solute to or from the blood can be controlled.

Potassium reservoir 307 can be fluidly connected to the dialysate flow loop and contain a source of potassium ions. In any embodiment of the first, second, or third aspects of the invention, the potassium reservoir 307 can contain a concentrated solution of potassium. Potassium can be added to the dialysate by operation of potassium pump 308 in order to achieve a desired concentration of potassium in the dialysate. The desired concentration of the potassium can be determined as described herein, and the potassium pump can be controlled to achieve the determined potassium concentration of the dialysate.

Fluid removal from the patient can be controlled by an ultrafiltrate system, comprising an ultrafiltration pump 305 and ultrafiltrate reservoir 304 fluidly connected to the dialysis flow loop. The ultrafiltration pump 305 can control the net fluid movement between the patient and the dialysate flow loop. Ultrafiltration pump 305 can be operated to draw fluid out of the dialysate flow loop 301 and into the ultrafiltrate reservoir 304. This will cause a net movement of fluid across the dialyzer 309 from the patient to the dialysate flow loop 301, thereby removing fluid from the patient. In any embodiment of the first, second, or third aspects of the invention, ultrafiltration pump 305 can also be operated to move fluid from ultrafiltrate reservoir 304 to the dialysate flow loop 301, providing a net movement of fluid across the dialyzer 309 from the dialysate flow loop 301 to the patient. In any embodiment of the first, second, or third aspects of the invention, movement of fluid between the dialysate flow loop 301 and ultrafiltrate reservoir 304 can be controlled by multiple pumps, wherein each pump can move fluid in a single direction.

Dialysate regeneration module 303 can be utilized to remove waste products from the dialysate. In any embodiment of the first, second or third aspects of the invention, dialysate regeneration module 303 can be a sorbent cartridge, which can contain sorbent materials that act to remove solutes from the dialysate in order to regenerate the dialysate. In any embodiment of the first, second or third aspects of the invention, dialysate regeneration module 303 can be any system known in the art capable of regenerating dialysate so that the dialysate can be circulated back to the dialyzer 309. In any embodiment of the first, second, or third aspects of the invention, a potassium sensor 306 can be included in the dialysate flow loop in order to monitor the concentration of potassium in the dialysate. The potassium monitor can be used to ensure that the proper potassium prescription is actually being used. In any embodiment of the first, second, or third aspects of the invention, a second potassium sensor (not shown) can be included downstream of the dialyzer. The difference between the potassium concentration prior to the dialysate reaching the dialyzer and the potassium concentration after the dialysate passes through the dialyzer can be used to calculate the potassium concentration of the patient. This allows continuous monitoring of the potassium concentration of the patient, and can allow for adjustment of the potassium or ultrafiltration prescription during dialysis in response to changes in patient potassium levels.

Although the system shown in FIG. 3 is a regenerative dialysis system, wherein the dialysate is regenerated after passing through the dialyzer 309, one of ordinary skill in the art will understand that, in any embodiment of the first, second, or third aspects of the invention, any dialysis system can be used, including single pass dialysis. In any embodiment of the first, second, or third aspects of the invention, the potassium concentration of the dialysate can be set by using pre-made dialysate having a specified potassium concentration. In any embodiment of the first, second, or third aspects of the invention, the system can comprise control electronics configured to control the pump rates of the ultrafiltration pump and/or the potassium pump, and thereby control the ultrafiltration amount and the potassium concentration in the dialysate. In any embodiment of the first, second, or third aspects of the invention, a processor or computer system can be included to calculate the risk scores, set the dialysis prescription and transmit instructions to the control electronics for controlling the pumps of the system. In any embodiment of the first, second or third aspects of the invention, the processor can be configured to obtain the potassium concentration in the patient and the amount of fluid removed from the patient and to calculate a second risk score based on these values monitored during dialysis. As explained, the potassium concentration in the patient can be determined during dialysis by a blood analysis using a ion selective electrode or a flame photometer, by use of an implantable loop recorder, implantable defibrillator, implantable cardiac monitor or by any other method known in the art. The processor can be configured to calculate an updated ultrafiltration prescription and/or potassium prescription based on changes in the risk score due to deviations from the originally set prescription. In any embodiment of the first, second, or third aspects of the invention, the processor can be configured to continuously receive or repeatedly receive the potassium concentration of the patient and/or the amount of fluid removed from the patient, and to continuously or repeatedly calculate an updated ultrafiltration prescription and/or updated potassium prescription based on the potassium concentration of the patient or amount of fluid removed from the patient.

As explained, in any embodiment of the first, second, or third aspects of the invention, the potassium concentration of the dialysate can be changed during a dialysis session. This change can be made manually, such as by changing the dialysate being used, or can be made in an automated fashion. In any embodiment of the first, second, or third aspects of the invention, a separate potassium feed solution can be provided. This potassium feed solution, similar to the potassium reservoir 307 and pump 308 of the system illustrated in FIG. 3, can be modulated as needed to modify the potassium concentration of the dialysate. In any embodiment of the first, second, or third aspects of the invention, the potassium feed solution can be turned on or off as desired throughout the dialysis session, thereby changing the potassium concentration in the dialysate. For example, the potassium feed solution can be turned on during a first portion of a dialysis session, providing a dialysate with a higher potassium concentration, and turned off during a second portion of the dialysis session, providing a dialysate with a lower potassium concentration. One of skill in the art will understand that the potassium feed can be modified in a number of ways to provide maximum flexibility in the potassium concentration of the dialysate. As explained, the modulation of the potassium feed can be controlled based on the measured potassium concentration changes in the patient or at predetermined times. One of skill in the art will understand that the modulation of the potassium feed can be conducted in a similar fashion to sodium profiling, which predetermines automated changes in sodium concentration throughout a dialysis session.

Calculation of Risk Scores

A prospective observational study was conducted to characterize the type and frequency of arrhythmias in patients receiving hemodialysis. 66 patients were implanted in the study. Data from each dialysis session, in addition to pre and post-session blood chemistries were collected bi-weekly for the first four weeks, and weekly for the following 22 weeks. Cardiac data from implantable cardiac monitoring systems were used to continuously monitor cardiac rhythm, heart rate and activity. The data from the cardiac monitoring system was collected concurrently with the hemodialysis treatment data over six months. All cardiac events were reviewed and adjudicated. Clinically significant arrhythmias (CSA) were defined to include bradycardia of ≤40 bpm for ≥6 seconds; asystole≥3 seconds; sustained ventricular tachycardia of ≥130 bmp for ≥30 seconds and symptomatic arrhythmias. Other documented arrhythmias, referred to as reviewer confirmed arrhythmias (RCA) included arrhythmias that do not meet the CSA arrhythmia definitions, atrial fibrillation and sinus tachycardia of >130 bpm. During the six months, 44 of the enrolled patients (67%) experienced a total of 1,720 CSA while 64 subjects (97%) had at least one of 12,686 RCA. During the study, a blood analysis was done in order to determine the serum potassium concentration of the patients. Because, during the study, blood was not routinely collected outside of the first dialysis session of the week, analysis was limited to the first dialysis session of the week. The time interval studied for the potassium analysis was the eight hours following the first dialysis session of the week. In any embodiment of the first, second, or third aspects of the invention, a time period for analysis of longer or shorter than 8 hours can be used, including between any of 1 hr to 2 days, 1 hr to 6 hrs, 1 hr to 8 hrs, 4 hrs to 12 hrs, 8 hrs to 1 day, or 8 hrs to 2 days.

A negative binomial mixed effects regression model was used to determine an estimate of the predicted arrhythmia rate as a function of the interdialytic change in potassium and the volume of fluid removed during the dialysis session. The negative binomial mixed effects regression model was chosen for this statistical analysis for several reasons, including that (1) the dependent variable is a count variable; (2) the dependent variable is ill-dispersed; (3) the observation time for subjects varied, thus the model is adjusted to account for the varying length of observation time per subject; and (4) there is correlation among repeated measures per subject; i.e., each subject is represented by multiple sessions in the analysis, so a random subject intercept is included. One of ordinary skill in the art will understand that alternative models, including but not limited to Poisson and zero-inflated negative binomial mixed regression models, could be used in place of the negative binomial mixed effects regression model. SAS 9.3 was used to model the data using proc GLIMMIX via maximum likelihood with the default canonical log link function. Gauss-Hermite Quadrature was used for likelihood estimation because the model does not have a closed form solution.

Table 1 illustrates the observed results for intradialytic changes in potassium from the study. In Table 1, N refers to the number of observations, the Mean refers to the mean values observed during the study. Min refers to the minimum value observed in the study for each entry, Max refers to the maximum value observed for each entry, and $25^{th}$ Pctl and $75^{th}$ Pctl refer to the values for each entry relating to the $25^{th}$ and $75^{th}$ percentiles for each entry, respectively.

TABLE 1

| Variable | N | Mean | Std Dev | Median | Min | 25th Pctl | 75th Pctl | Max |
|---|---|---|---|---|---|---|---|---|
| Pre-dialysis Potassium | 1376 | 4.901454 | 0.780386 | 4.8 | 2.8 | 4.3 | 5.4 | 8.7 |
| Post-dialysis Potassium | 1352 | 3.629586 | 0.613732 | 3.5 | 2.6 | 3.3 | 3.8 | 8.7 |
| Intradialytic Change in Potassium | 1332 | −1.26381 | 0.76329 | −1.3 | −4.5 | −1.7 | −0.8 | 3.2 |

As shown in Table 1, 50% of the observations shows a pre-dialysis potassium level of between 4.3 and 5.4 mEq/L, a post-dialysis potassium level of between 3.3 and 3.8 mEq/L, and an intradialytic change in potassium of between −1.7 and −0.8 mEq/L. The values falling between the 25$^{th}$ and 75$^{th}$ percentiles were used in the modeling.

Table 2 shows the observed results for the amount of fluid removed from the patients during each session of the study.

TABLE 2

| Variable | N | Mean | Std Dev | Median | Min | 25th Pctl | 75th Pctl | Max |
|---|---|---|---|---|---|---|---|---|
| Volume Removed (L) | 1592 | 3.367023 | 1.347978 | 3.3 | −0.9 | 2.5 | 4.2 | 7.7 |

As illustrated in Table 2, 50% of the observations showed between 2.5 and 4.2 L of fluid removed from the patient during each dialysis session. The values falling between the 25$^{th}$ and 75$^{th}$ percentiles were used in the modeling.

Figure 4:
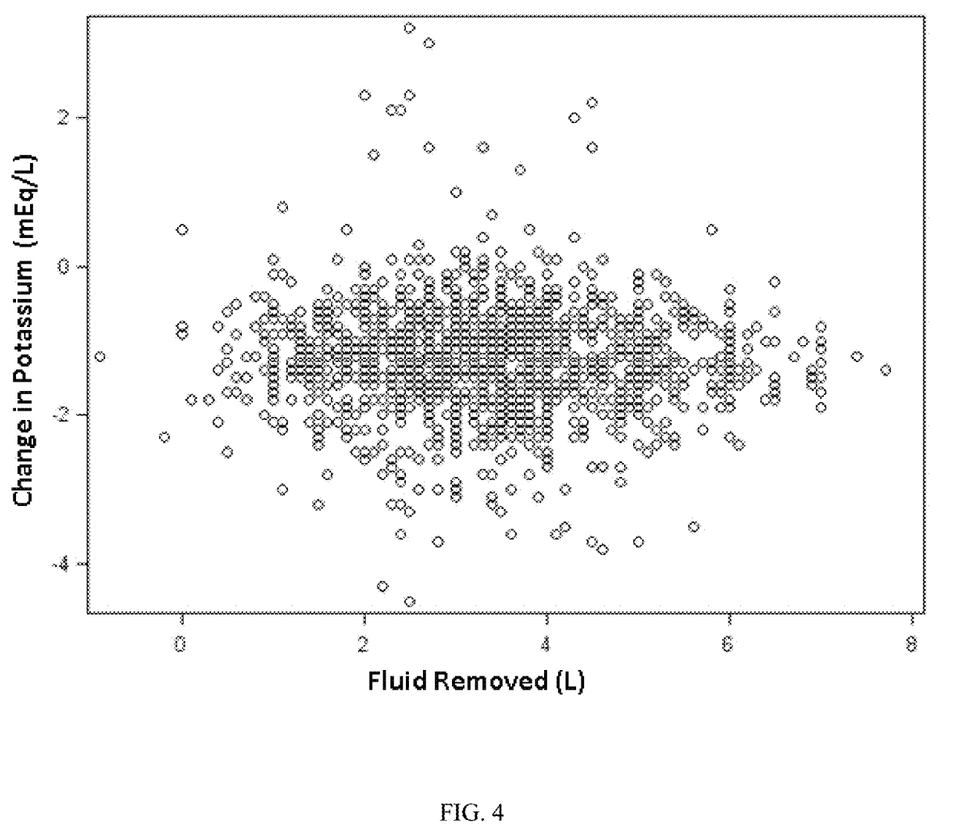
FIG. 4 is a scatter plot showing the changes in potassium concentration and amounts of fluid removed from patients during a prospective study.

FIG. 4 is a scatter plot showing the change in potassium, depicted as mEq/L, and the fluid volume removed from the patients, depicted as L, for each observation. FIG. 4 provides the distribution of the values summarized in Tables 1 and 2.

The solutions obtained from the modeling are shown in Table 3.

TABLE 3

Solutions for Fixed Effects

| Effect | Estimate | Standard Error | DF | t Value | Pr > |t| |
|---|---|---|---|---|---|
| Intercept | −4.4918 | 0.3254 | 65 | −13.80 | <.0001 |
| Change_Potassium | −0.3252 | 0.1365 | 1253 | −2.38 | 0.0174 |
| VolumeRemoved | −0.2050 | 0.2069 | 1253 | −0.99 | 0.3218 |
| Change_Po * VolumeRemo | −0.2636 | 0.1174 | 1253 | −2.24 | 0.0250 |

As shown in Table 3, the interaction between change in potassium level and the volume removed is statistically significant, with a P value equal to 0.0250. Using the solutions shown in Table 3, an estimate for the frequency of cardiac arrhythmia based on changes in potassium level and amount of fluid removed during dialysis can be created, as shown in Table 4.

TABLE 4

| Label | Estimate | Lower | Upper | Mean | Standard Error Mean | Lower Mean | Upper Mean |
|---|---|---|---|---|---|---|---|
| Change_Potassium = −2 VolumeRemoved = −2.3 | −4.1635 | −4.8673 | −3.4598 | 0.01555 | 0.005579 | 0.007694 | 0.03144 |
| Change_Potassium = −2 VolumeRemoved = 3.3 | −3.8414 | −4.4195 | −3.2632 | 0.02146 | 0.006326 | 0.01204 | 0.03827 |
| Change_Potassium = −2 VolumeRemoved = 4.3 | −3.5192 | −4.1693 | −2.8691 | 0.02962 | 0.009816 | 0.01546 | 0.05675 |
| Change_Potassium = −1 VolumeRemoved = 2.3 | −4.2252 | −4.8854 | −3.5649 | 0.01462 | 0.004921 | 0.007556 | 0.02830 |
| Change_Potassium = −1 VolumeRemoved = 3.3 | −4.1666 | −4.7136 | −3.6196 | 0.01550 | 0.004323 | 0.008973 | 0.02679 |
| Change_Potassium = −1 VolumeRemoved = 4.3 | −4.1080 | −4.6960 | −3.5201 | 0.01644 | 0.004927 | 0.009132 | 0.02960 |
| Change_Potassium = 0 VolumeRemoved = 2.3 | −4.2868 | −5.0512 | −3.5223 | 0.01375 | 0.005357 | 0.006401 | 0.02953 |
| Change_Potassium = 0 VolumeRemoved = 3.3 | −4.4918 | −5.1303 | −3.8534 | 0.01120 | 0.003645 | 0.005915 | 0.02121 |
| Change_Potassium = 0 VolumeRemoved = 4.3 | −4.6969 | −5.4453 | −3.9484 | 0.009124 | 0.003481 | 0.004316 | 0.01929 |

For simplicity, the volume removed in each entry of Table 4 is shown in liters, and the change in potassium is shown in mEq/L. The mean values presented in Table 4 are the antilog of the estimates from the modeling, and represent an estimated rate of arrhythmias per hour. Using the data presented in Tables 1-4, one of ordinary skill in the art can create an algorithm that relates the changes in potassium levels and the amount of fluid volume removed to the frequency of arrhythmia. In any embodiment of the first, second or third aspects of the invention, the system can use this algorithm to calculate the risk scores for arrhythmia. In any embodiment of the first, second, or third aspects of the invention, the algorithm can calculate the risk score as a linear or non-linear function of the changes in fluid volume and potassium concentration in the patient.

Figure 5:
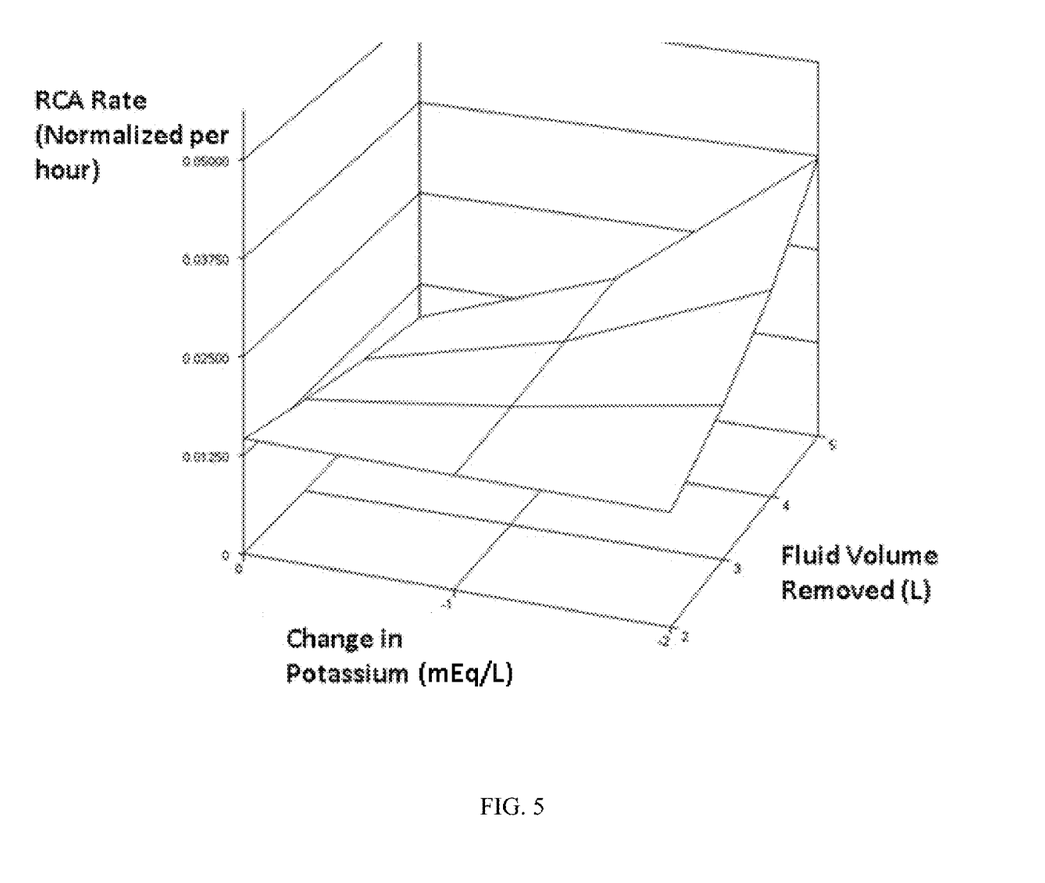
FIG. 5 is a 3-D graph of the estimated arrhythmia rate due to intradialytic potassium changes and the amount of fluid removed.

FIG. 5 is a graphical representation of the data in Table 4. FIG. 5 is a 3-D graph of the estimated arrhythmia rate due to intradialytic potassium changes and the amount of fluid removed. As shown in FIG. 5, as the magnitude of the changes in potassium concentration is increased, the rate of arrhythmia likewise increases. Further, as the amount of fluid removed is increased, the rate of arrhythmia is increased.

In any embodiment of the first, second, or third aspects of the invention, the dialysis prescription can be set according to the model described, or any other statistical model capable of estimating arrhythmias based on intradialytic changes in potassium and the amount of fluid removed. As illustrated in FIG. 2, the amount of fluid removed and desired change in potassium level can be compared to the statistical model, and the system can determine whether the estimated arrhythmia rate due to these factors is above some unacceptable level. In any embodiment of the first, second, or third aspects of the invention, the system can include a predetermined value for an estimated arrhythmia rate, and the system can optimize the dialysis prescription in order to ensure that the estimated arrhythmia rate is below this predetermined value. In any embodiment of the first, second, or third aspects of the invention, the predetermined value can manage the risk of arrhythmia to be estimated at or below 0.02 arrhythmias per hour. In any embodiment of the first, second, or third aspects of the invention, the predetermined value can manage the risk of arrhythmia to be estimated at between any of 0.01 and 0.03, 0.01 and 0.015, 0.01 and 0.02, 0.015 and 0.03, or 0.02 and 0.03 arrhythmias estimated per hour. The system can automatically adjust the dialysis prescription until the risk score for arrhythmia is below the predetermined value. In any embodiment of the first, second, or third aspects of the invention, the system can comprise a manual override, allowing dialysis to be conducted even if the risk score for arrhythmia is over some predetermined value, allowing the caregiver to make a separate determination in each case whether the risk of arrhythmia is acceptable.

In any embodiment of the first, second, or third aspects of the invention, the risk score for arrhythmia of each patient can be calculated prior to a dialysis session using the statistical model as described herein. In any embodiment of the first, second, or third aspects of the invention, the risk score for arrhythmia can instead be determined using a lookup table. A lookup table can be created that includes the data used in the statistical model, correlating the frequency of arrhythmia with intradialytic changes in potassium and the amount of fluid removed. The system can utilize the lookup table, starting with a desired potassium concentration change and a desired fluid removal amount, and determine the frequency of arrhythmia due to these changes. If the lookup table provides a high frequency of arrhythmia for a given set of parameters, the system can adjust either or both of the desired potassium concentration change and the desired fluid volume change until the data in the lookup table provides a frequency of arrhythmia below some predetermined value.

One of skill in the art will understand that other variables beyond changes in potassium and the fluid volume removed from a patient may influence the rate or risk factor for arrhythmia. For example, certain patients may be more susceptible to arrhythmia than other patients. In any embodiment of the first, second, or third aspects of the invention, the calculation of the risk score can take into account one or more other factors beyond changes in potassium and fluid volume. However, in any embodiment of the first, second, or third aspects of the invention, the calculation of the risk score can be at least based in part on changes in potassium levels and/or fluid volume removed.

One skilled in the art will understand that various combinations and/or modifications and variations can be made in the described systems and methods depending upon the specific needs for operation. Moreover features illustrated or described as being part of an aspect of the invention may be used in the aspect of the invention, either alone or in combination, or follow a preferred arrangement of one or more of the described elements

We claim:

1. A method, comprising the steps of:
measuring a change in potassium concentration of a patient during dialysis to calculate a risk score for cardiac arrhythmia during or after dialysis;
measuring a volume of fluid removed from the patient during dialysis; and
calculating the risk score for arrhythmia for the patient; wherein the risk score is indicative of a probability of cardiac arrhythmia.

2. The method of claim 1, further comprising the step of calculating a change in potassium concentration during dialysis based on a pre-dialysis potassium concentration and a post-dialysis potassium concentration.

3. The method of claim 2, wherein at least one of the pre-dialysis potassium concentration and post-dialysis potassium concentration is measured by changes in an ECG for the patient.

4. The method of claim 2, wherein at least one of the pre-dialysis potassium concentration and post-dialysis potassium concentration is measured by a potassium monitor connected to a patient or extracorporeal flow loop.

5. The method of claim 2, wherein the potassium concentration of the patient is measured using a potassium sensor upstream of a dialyzer of a dialysis system and a potassium sensor downstream of the dialyzer.

6. The method of claim 1, wherein the step of calculating a risk score for arrhythmia uses an algorithm.

7. The method of claim 1, further comprising the step of measuring the change in potassium concentration of a patient using any one of an implantable loop recorder, implantable defibrillator, implantable cardiac monitor, blood analysis, ion-selective electrode, or flame photometer.

8. The method of claim 1, further comprising the step of increasing monitoring of the patient after dialysis if the risk score for arrhythmia is above a preset threshold.

9. The method of claim 8, wherein the predetermined threshold is between any of 0.01 and 0.03, 0.01 and 0.015, 0.01 and 0.02, 0.015 and 0.03, or 0.02 and 0.03 arrhythmias estimated per hour.

10. The method of claim 8, wherein the predetermined threshold is less than or equal to 0.02 instances of arrhythmia per hour.

11. The method of claim 1, wherein the step of calculating a risk score for arrhythmia uses a lookup table.

12. The method of claim 1, wherein the step of measuring a fluid volume removed from the patient during dialysis uses impedance measurements or a comparison of the patient's weight to a known or estimated dry weight of the patient.

13. The method of claim 1, wherein the step of calculating a risk score for arrhythmia uses a linear or non-linear function of the change in potassium concentration of a patient during dialysis and volume of fluid removed from the patient during dialysis.

14. The method of claim 1, wherein the step of calculating a risk score for arrhythmia uses a statistical model.

15. The method of claim 14, wherein the statistical model uses negative binomial mixed effects regression model, a Poisson model, or a zero-inflated negative binomial mixed regression model.

16. The method of claim 1, wherein the step of calculating a risk score for arrhythmia uses at least one factor in addition to the change in potassium concentration of a patient during dialysis and the volume of fluid removed from the patient during dialysis.

17. The method of claim 16, further comprising the step of averaging the pre-dialysis potassium concentration or the post-dialysis potassium concentration measured by the at least two different methods.

18. The method of claim 1, wherein at least one of the pre-dialysis potassium concentration and the post-dialysis potassium concentration are measured using at least two different methods.

19. The method of claim 18, wherein the dialysis system is a regenerative dialysis system.

20. The method of claim 1, wherein the method is performed by a processor of a dialysis system.

* * * * *